United States Patent
Green et al.

(10) Patent No.: US 6,190,401 B1
(45) Date of Patent: *Feb. 20, 2001

(54) DEVICE FOR APPLYING A MENISCAL STAPLE

(75) Inventors: David T. Green, Westport; Robert J. Geiste, Milford; Wayne C. Person, Newtown, all of CT (US)

(73) Assignee: United States Surgical Corporation, Norwalk, CT (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/999,812

(22) Filed: Jul. 2, 1997

Related U.S. Application Data

(60) Continuation of application No. 08/449,175, filed on May 24, 1995, now abandoned, which is a division of application No. 08/345,539, filed on Nov. 28, 1994, now Pat. No. 5,643,319, which is a continuation of application No. 07/947,753, filed on Sep. 21, 1992, now abandoned, which is a continuation-in-part of application No. 07/699,991, filed on May 13, 1991, now Pat. No. 5,269,783.

(51) Int. Cl.[7] .................................................. A61B 17/06
(52) U.S. Cl. .......................... 606/224; 606/219; 606/221; 606/222; 227/902
(58) Field of Search ............................... 606/72, 75, 219, 606/77, 221, 222, 224, 225, 228; 227/902

(56) References Cited

U.S. PATENT DOCUMENTS

| 2,075,508 | 3/1937 | Davidson . |
| 2,199,025 | 4/1940 | Conn . |
| 2,802,468 | 8/1957 | Everett . |

(List continued on next page.)

FOREIGN PATENT DOCUMENTS

| 314412 | 5/1989 | (EP) . |
| 390613 | 10/1990 | (EP) . |
| 2118474 | 11/1983 | (GB) . |
| 1197657 | * 12/1985 | (SU) ...................................... 606/75 |
| 8603396 | 6/1986 | (WO) . |
| 8701270 | 3/1987 | (WO) . |

OTHER PUBLICATIONS

Daniel F. Justin, "A Needle Guided Resorbable Staple for Arthroscopic Meniscal Repair," Unversity of Central Florida, Department of Mechanical Engineering, pp. 127–130.

Vincent J. DiStefano et al., "A Technique of Arthroscopic Meniscoplasty", *Orthopedics,* Sep. 1983, vol. 6, No. 9, pp. 1135–1140.

(List continued on next page.)

*Primary Examiner*—Michael A. Brown
*Assistant Examiner*—Benjamin K. Koo

(57) ABSTRACT

An apparatus for inserting a staple into torn tissue such as the meniscus of the knee. The apparatus includes a pair of shafts individually movable in a longitudinal directing which are actuable from a handle mechanism. The shafts are movable sequentially so that the shafts disjunctively advance the prongs of the staple which is releasably held adjacent distal end portions of the shafts. A further embodiment of the device consists of a pair of needles detachably secured to a pair of anchoring members having a plurality of barb-like projections extending outwardly therefrom. The anchoring members are joined by a suture which connects adjacent the trailing ends of the anchoring members opposite the penetration end of the needles. The needles are engaged with the anchoring members to transmit a first pushing force applied to the needles to advance the anchoring members into the tissue, and are releasable from their engagement with the anchoring members responsive to a second pulling force applied to the needles in a direction opposite the pushing direction.

10 Claims, 13 Drawing Sheets

U.S. PATENT DOCUMENTS

| Number | Date | Name | Ref |
|---|---|---|---|
| 2,968,041 | 1/1961 | Skold . | |
| 3,123,077 | 3/1964 | Alcamo . | |
| 3,570,497 | 3/1971 | Lemole . | |
| 3,875,946 | 4/1975 | Duncan . | |
| 3,890,975 | 6/1975 | McGregor . | |
| 3,976,079 | 8/1976 | Samuels et al. . | |
| 3,981,307 | 9/1976 | Borysko . | |
| 4,265,226 | 5/1981 | Cassimally . | |
| 4,344,193 | 8/1982 | Kenny . | |
| 4,359,053 | 11/1982 | Benjamin . | |
| 4,462,395 | 7/1984 | Johnson . | |
| 4,549,545 | 10/1985 | Levy . | |
| 4,635,637 | 1/1987 | Schreiber . | |
| 4,649,920 | 3/1987 | Rhum . | |
| 4,696,300 | 9/1987 | Anderson . | |
| 4,712,550 | 12/1987 | Sinnett . | |
| 4,738,255 | 4/1988 | Goble et al. . | |
| 4,741,330 | 5/1988 | Hayhurst . | |
| 4,781,190 | 11/1988 | Lee . | |
| 4,790,303 * | 12/1988 | Steffee | 606/72 |
| 4,790,304 * | 12/1988 | Rosenberg | 606/72 |
| 4,841,960 | 6/1989 | Garner . | |
| 4,858,603 | 8/1989 | Clemow . | |
| 4,869,242 | 9/1989 | Galluzzo . | |
| 4,873,976 | 10/1989 | Schreiber . | |
| 4,875,479 | 10/1989 | Belykh et al. . | |
| 4,895,148 * | 1/1990 | Bays et al. | 606/213 |
| 4,901,712 | 2/1990 | Voegell et al. . | |
| 4,924,865 * | 5/1990 | Bays et al. | 606/77 |
| 4,926,860 | 5/1990 | Stice et al. . | |
| 4,950,285 | 8/1990 | Wilk . | |
| 4,976,715 * | 12/1990 | Bays et al. | 606/77 |
| 4,981,149 | 1/1991 | Yoon et al. . | |
| 4,994,065 | 2/1991 | Gibbs . | |
| 4,997,436 | 3/1991 | Oberlander . | |
| 5,002,562 | 3/1991 | Oberlander . | |
| 5,035,707 | 7/1991 | Korthoff . | |
| 5,053,047 | 10/1991 | Yoon . | |
| 5,059,206 | 10/1991 | Winters . | |
| 5,102,421 | 4/1992 | Anspach, Jr. . | |
| 5,154,189 | 10/1992 | Oberlander . | |
| 5,269,783 * | 12/1993 | Sander | 606/72 |

OTHER PUBLICATIONS

Willima G. Clancy, Jr. et al., "Arthroscopic Meniscal Repair," *Orthopedics,* Sep. 1983, vol. 6, No. 9, pp. 1125–1129.

Charles E. Henning, "Arthroscopic Repair of Meniscus Tears," *Orthopedics,* Sep. 1983, vol. 6, No. 9, pp. 1130–1132.

A brochure entitled "The Meniscal Anchor" from GMI, Inc.

Ethicon Brochure, 1966, 4 pages.

EPO Search Report from Corresponding European Patent Application No. 93114580.9.

* cited by examiner

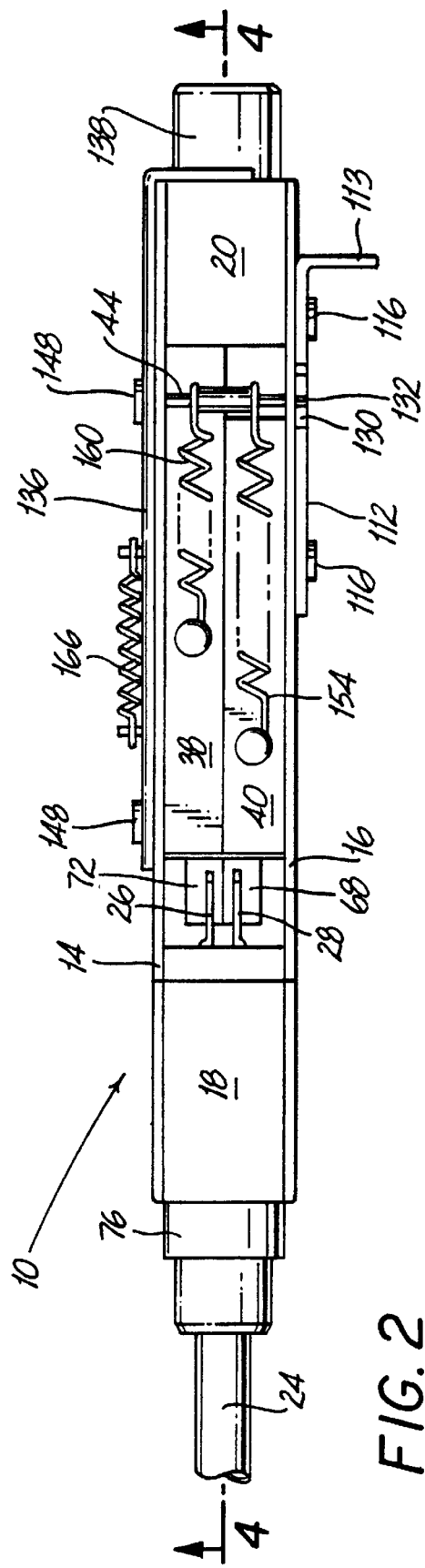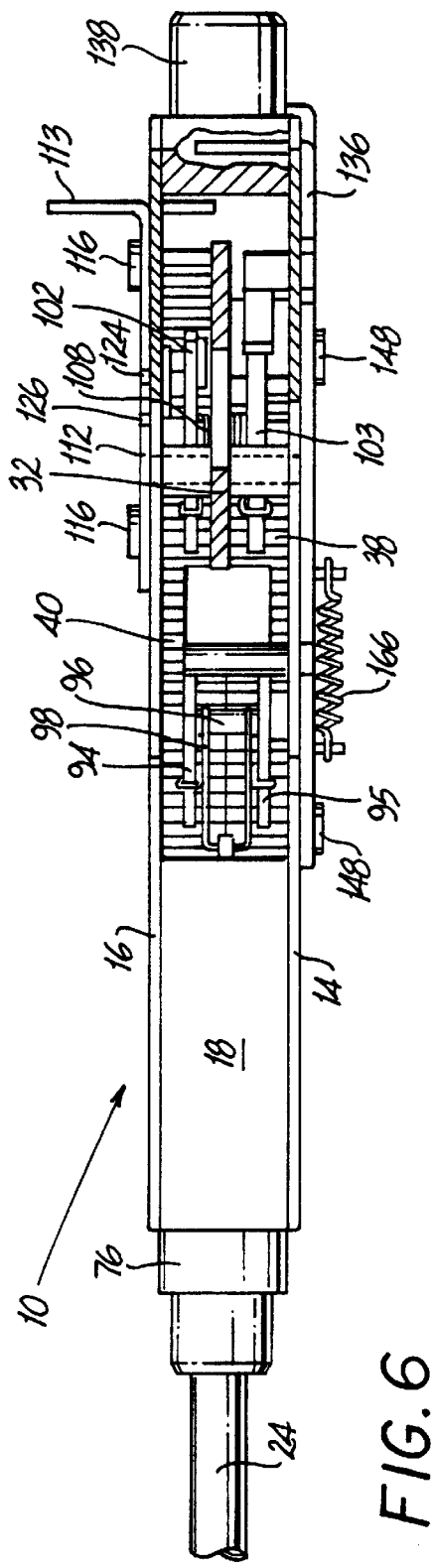
FIG. 2
FIG. 6

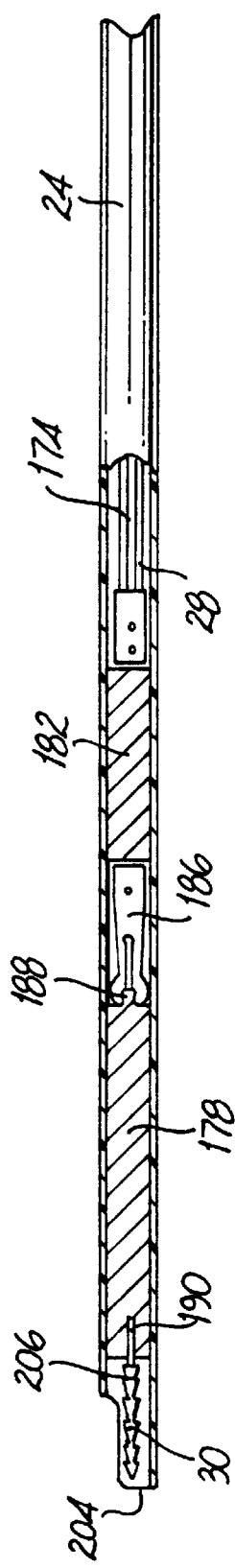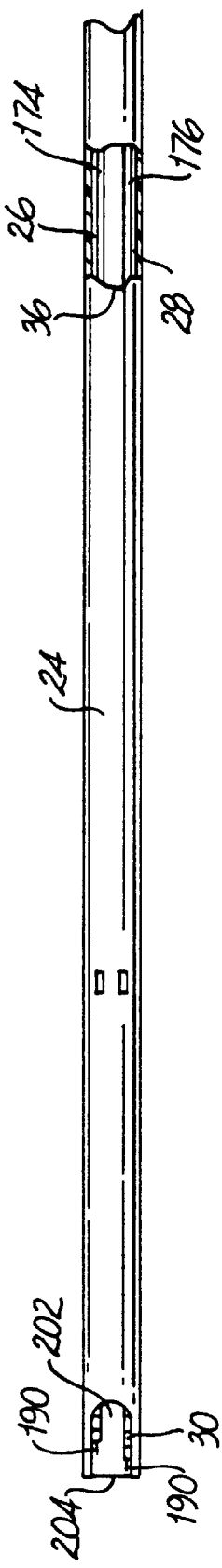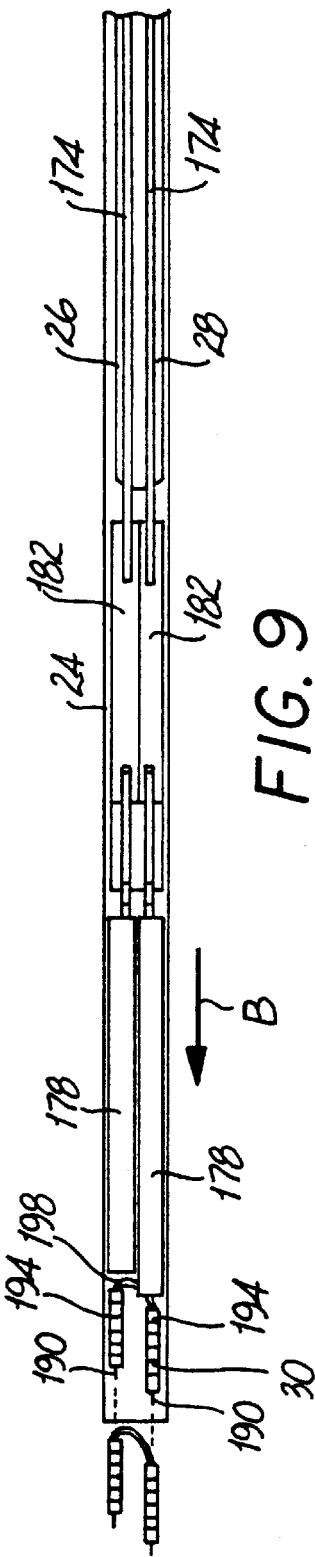

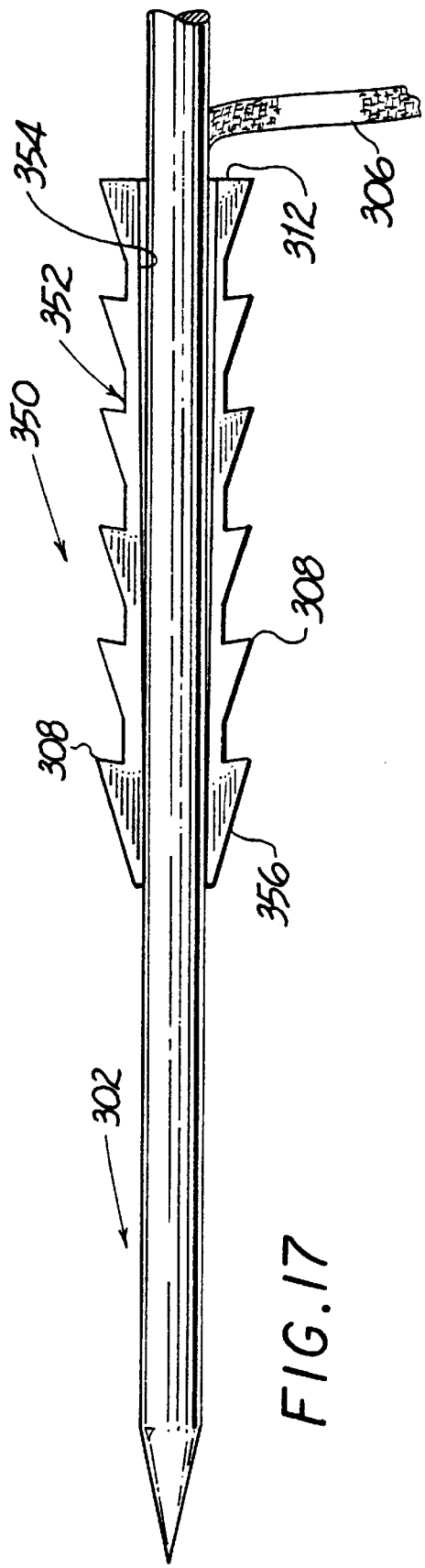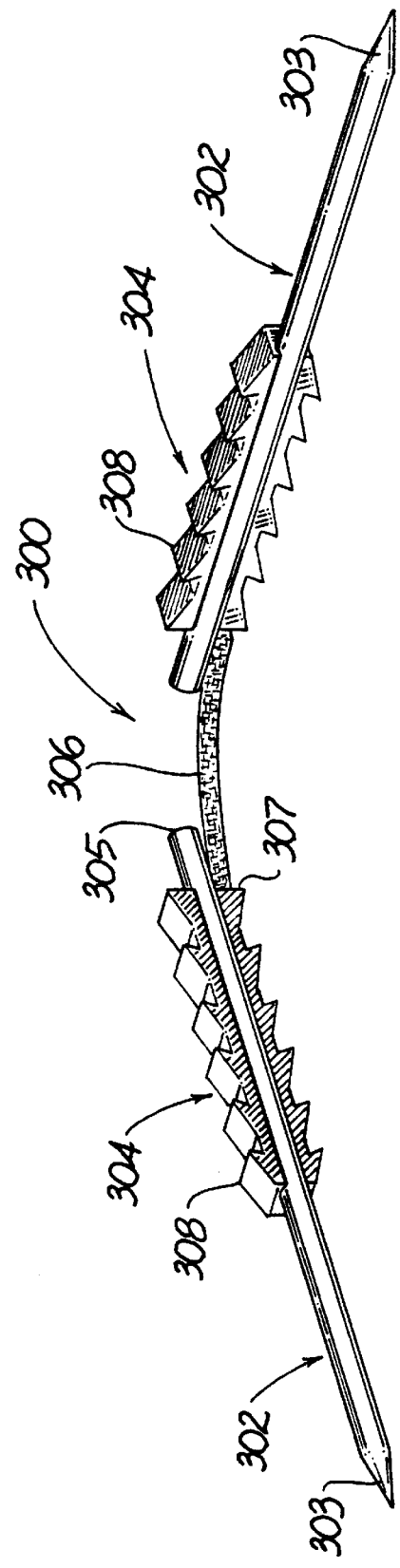

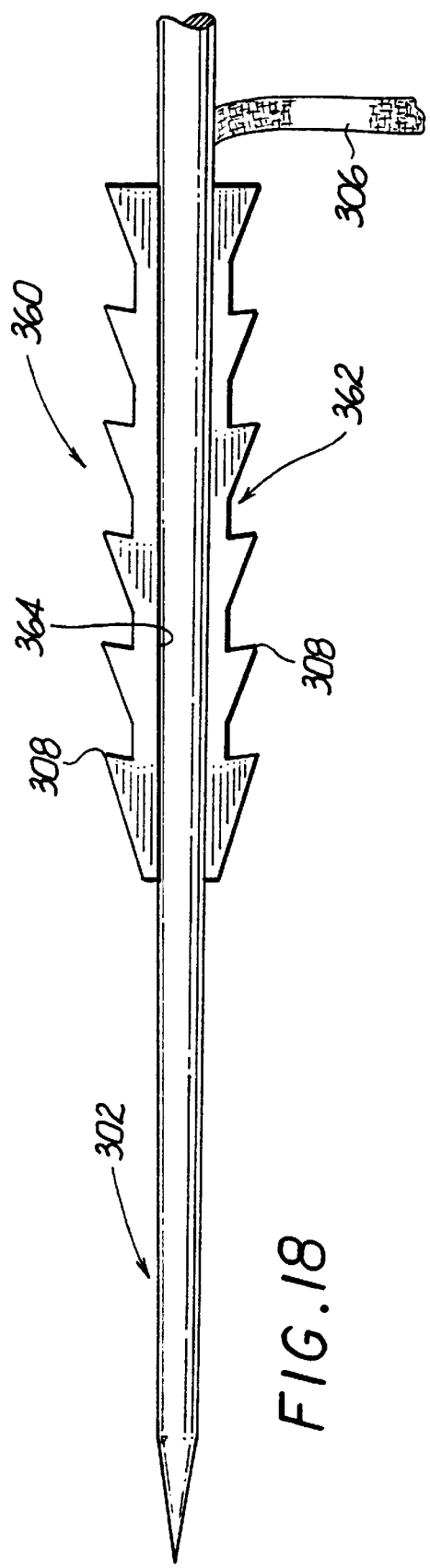
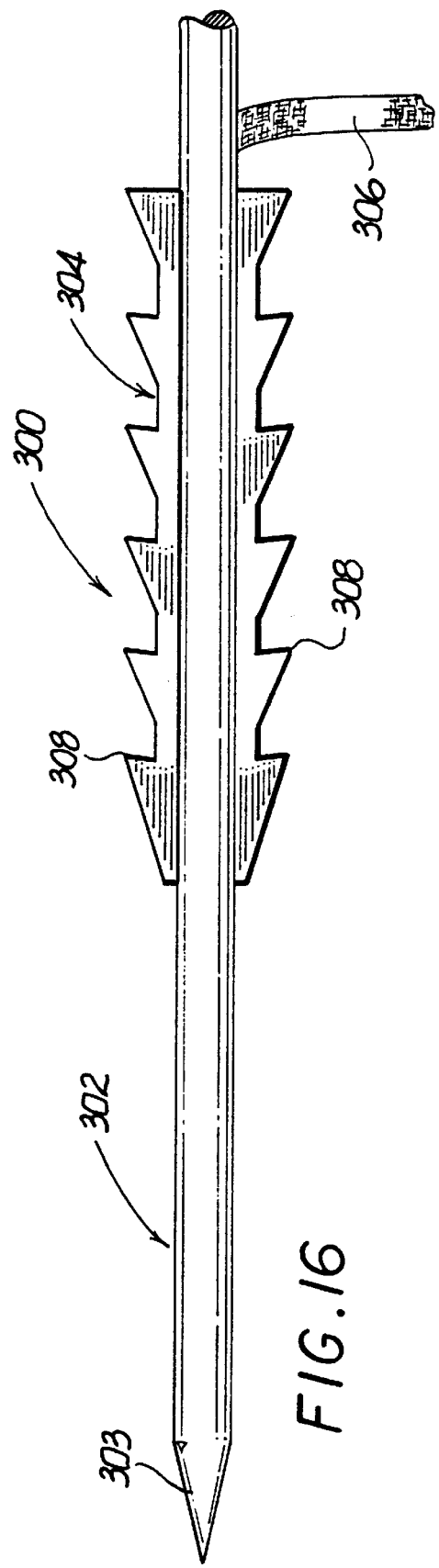

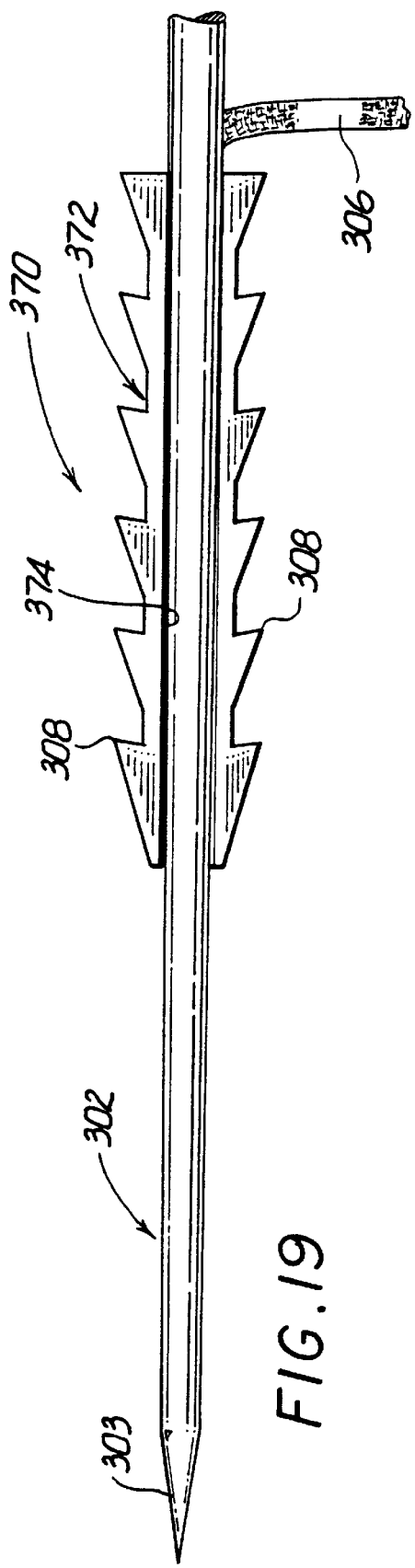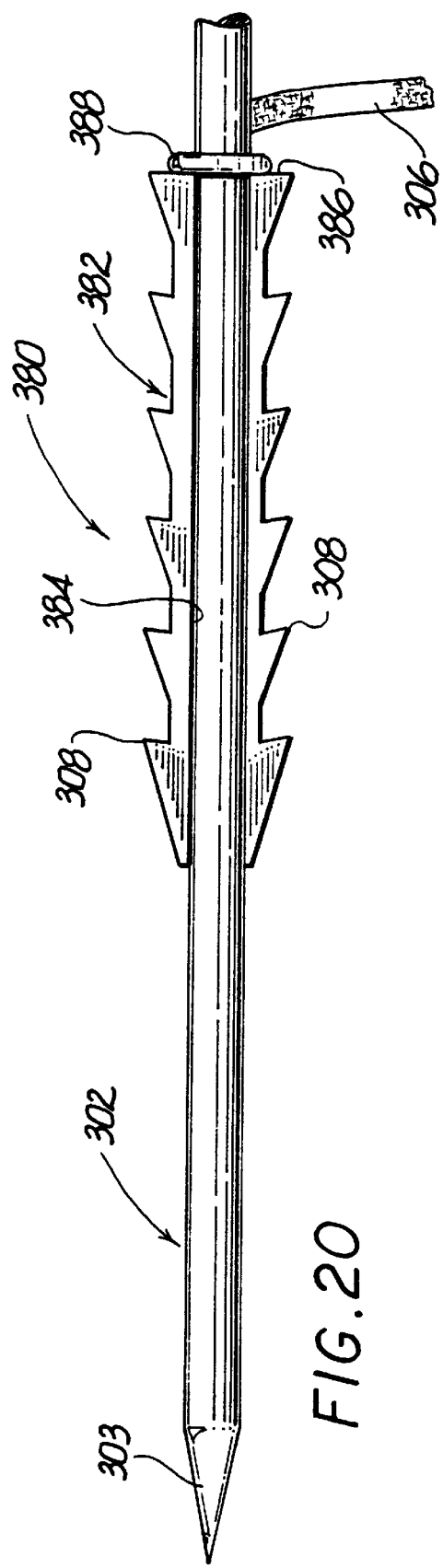

DEVICE FOR APPLYING A MENISCAL STAPLE

CROSS REFERENCE TO RELATED APPLICATION

This is a continuation of application Ser. No. 08/449,175 filed on May 24, 1995, now abandoned, which is a divisional of Ser. No. 08/345,539 filed on Nov. 28, 1994, now U.S. Pat. No. 5,643,319 which is a continuation of Ser. No. 07/947,753 filed on Sep. 21, 1992, now abandoned which is a CIP of Ser. No. 07/699,991 filed on May 13, 1991 now U.S. Pat. No. 5,269,783.

BACKGROUND OF THE INVENTION

1. Field of the Invention

The present invention relates to the field of laparoscopic or endoscopic surgery, and more particularly to a device for advancing a surgical staple into torn tissue such as the meniscus of the knee for repairing the torn meniscus.

2. Discussion of the Prior Art

A technique has been developed using arthroscopic instruments which provides for meniscal repair through the use of a pair of surgical needles which are inserted through cannuli into the knee on opposite sides of the tear in the meniscus to be repaired. The needles are linked by a single suture which is pushed down through the cannuli and across the tear. An incision is made in the skin at the point where the needle exit the knee joint so that the leading end of each needle may be grasped and pulled through the joint. The ends of the sutures are then grasped after the needles are removed from the suture ends and the suture is then tied outside the skin so that a horizontal suture is created in the meniscus. This procedure is repeated for placement of as many suture as necessary to repair the meniscus tear. This process is very time consuming, and the strength of the repair is dependent upon the tension created by the knot tied in the suture.

An additional procedure and instrument is known from U.S. Pat. No. 5,002,562, in which a barbed clip and instrument for applying the clip for repairing peripheral meniscal tears is disclosed. The instrument has a pair of opposed arcuate jaws which are shaped to hold a complementary-shaped curved surgical clip therebetween, such that the barbs of the clip are retained within notches in the jaws until the clip is inserted. The legs of the clip are typically joined by a flexible material, such as a suture. The jaws are biased in a normally open position, and as the jaws are pushed into the tissue, the jaws are scissored or closed together until they preferably overlap to move the legs of the clip together until they cross. The jaws are then reopened and backed out of the tissue, with the barbs of the clip retaining the clip in position in the tissue.

However, a disadvantage of such a device lies in the fact that the scissoring or cutting action of the jaws necessary to move the legs of the clip together may further damage the surrounding meniscal tissue. Consequently, there remains a need for a tool for applying tacks or staples which avoids incidental damage to the tissue during insertion of the staple. The need exists for a device for repairing torn tissue, such as the meniscus of the knee, which obviates the disadvantages encountered in the prior art and provides an efficient, suture-type device which expedites the surgical procedure and reduces the amount of precision necessary on the part of the surgeon during the procedure.

SUMMARY OF THE INVENTION

It is therefore an aim of the present invention to provide a tool which avoids any incidental damage to surrounding tissue during repair of torn tissue, such as a procedure for repair of the meniscus. The present invention provides such a tool for linearly inserting a resorbable staple into the mensicus. In order to insert the staple linearly, the tool includes longitudinally movable shaft members, which are advanced longitudinally to advance the staple held at the distal ends of the shafts linearly into the meniscus. To accomplish longitudinal movement of the shaft members, a pair of squeezable handles are provided which are movable toward one another to move the shafts distally to advance the staple linearly into the meniscus. Means are provided for translating movement of the handles into the linear advancement of the shaft members, in the form of a rack and pawl mechanism, which translates the pivotal motion of the handles toward each other to longitudinal motion to move the shafts distally.

The tool of the present invention provides for sequential advancement of the staple member in that the legs are advanced one at a time. A first leg is advanced into position in the tissue, followed by advancement of the second leg so that the flexible material is positioned across the tear in the meniscus. After the first leg is positioned in the tissue, the pawl member associated with the first shaft member is disengaged from its rack member to terminate further advancement of the first leg. The second leg member is then advanced into the tissue so that the suture material is positioned across the tear. The tool further includes means for releasing the shaft members after insertion of the staple to return the shafts to their original position so that the tool may be withdrawn from the surgical site.

In a second embodiment, the device for repairing torn tissue and muscles of the present invention comprises a pair of surgical needles, each of which is engaged with one of a pair of anchoring leg members, which essentially comprise absorbable rods having outwardly projecting barbs. Each anchoring leg member is secured adjacent a second end opposite the penetration end to an absorbable flexible material such as a suture which extends between the two anchoring leg members. The means of engagement between the needles and anchoring leg members allows for a first pushing force applied axially to the needles in a first direction to be transmitted to the anchoring leg members to advance the anchoring members into the torn tissue, while allowing for the release of the needles responsive to a second pulling movement applied in an opposite direction to the pushing force. The means of engagement between the needles and anchoring members may be provided by a frictional engagement between a channel in each of the anchoring members and the needles.

The tool of the present invention thus reduces the incidental trauma to tissue caused during the insertion of a staple by providing for linear insertion of the staple. The tool expedites the surgical process by providing for quick loading of the staple and insuring accurate placement at the tissue tear.

The staple member for use with the tool of the present invention preferably includes a pair of anchoring leg members constructed with a plurality of outwardly directed barb members along their length. The material of which the leg members are formed is preferably a substantially rigid bioresorbable material which allows for penetration of the legs into the meniscal tissue. The barb members permit forward penetration but restrict or prevent reverse movement of the barbs, thereby preventing the legs from backing out of the tissue after placement. Preferably, the leg members are formed by injection molding techniques.

The leg members include a longitudinal slot or channel which accepts a needle member which is positioned at the distal end of each shaft member of the tool of the present invention. The leg members are loaded onto the needles for placement into the tissue, such that the needles penetrate the tissue so that the leg members may be driven behind the needles into position. Preferably, the leg members are joined at their rearward ends by a flexible material such as a suture. After the leg members are secured in the tissue, the needles, and the tool, are withdrawn leaving the leg members and suture anchored in the tissue.

The needles for use with the invention may have a uniform cross section, with one of the needles being positioned in each channel. In order to provide a suitable engagement therebetween, each channel maybe provided with a narrower uniform cross section suitable to provide a frictional engagement with the needle so that a first pushing force applied axially to the needles is transmitted to the anchoring members to advance the anchoring members into the torn tissue, while a second pulling force applied in the opposite direction to the pushing force releases the needles from their engagement with the anchoring members.

With other embodiments, the needles may similarly have a uniform cross section, and each channel may taper or narrow to a suitable diameter less than the diameter of the needles. The needles may instead be tapered in the direction of their sharp, penetration tip, and each channel may have a uniform cross section. Alternatively, each of the channels may taper or narrow in the direction of the penetration end of the anchoring member, and each needle positioned therein may have a corresponding taper in the direction of its sharp, penetration tip. In a further alternative embodiment, each needle may be provided with a shoulder, and each channel may be provided with a uniform cross section somewhat wider than the needle positioned therein for longitudinal motion of the needle therein. In this embodiment, each anchoring member provides an abutment portion around the distal end of the channel against which the shoulder abuts to provide an abutting relationship to transmit the pushing force to the anchoring members while allowing for easy withdrawal of the needles from the anchoring members responsive to movement rearwards in a direction opposite the pushing force.

With each of the preferred embodiments, the barbs of the anchoring member have a tapered configuration towards the penetration end of the needles so that as the needles are pushed through the tissue, the barbs easily pass through the tissue with the needle. The configuration of the barbs is such that the anchoring members pass easily through the tissue in the forward direction, but are prevented from moving in the reverse direction. The barbs are provided to anchor the device in the tissue.

The connection between the anchoring members and the suture may include adhesives, swaging, crimping or the like. Preferably, both the suture and the anchoring members are constructed of a bioresorbable material.

BRIEF DESCRIPTION OF THE DRAWINGS

The foregoing features of the present invention will become more readily apparent and may be understood by referring to the following detailed description of an illustrative embodiment of device according to the present invention, taken in conjunction with the accompanying drawings, in which:

FIG. 2 illustrates a top cut-away view of the embodiment of FIG. 1;

FIG. 6 illustrates a bottom cut-away view taken along lines 6—6 of FIG. 3;

FIG. 7 illustrates a top detailed view of the distal end of the device of FIG. 1;

FIG. 8 illustrates a partially cut-away side view of the distal end of the device of FIG. 7;

FIG. 9 illustrates a cut-away top view of the distal end of the device of FIG. 7;

FIG. 10 illustrates a perspective view of an alternate embodiment of the device of the present invention;

FIG. 16 illustrates a side view of the embodiment of FIG. 10;

FIG. 17 illustrates a side view of another embodiment of the device of FIG. 10;

FIG. 18 illustrates a side view of a further embodiment of the device of FIG. 10;

FIG. 19 illustrates a side view of an additional embodiment of the device of FIG. 10;

FIG. 20 illustrates a side view of another embodiment of the device of FIG. 10;

DETAILED DESCRIPTION OF THE PREFERRED EMBODIMENT

Figure 1:
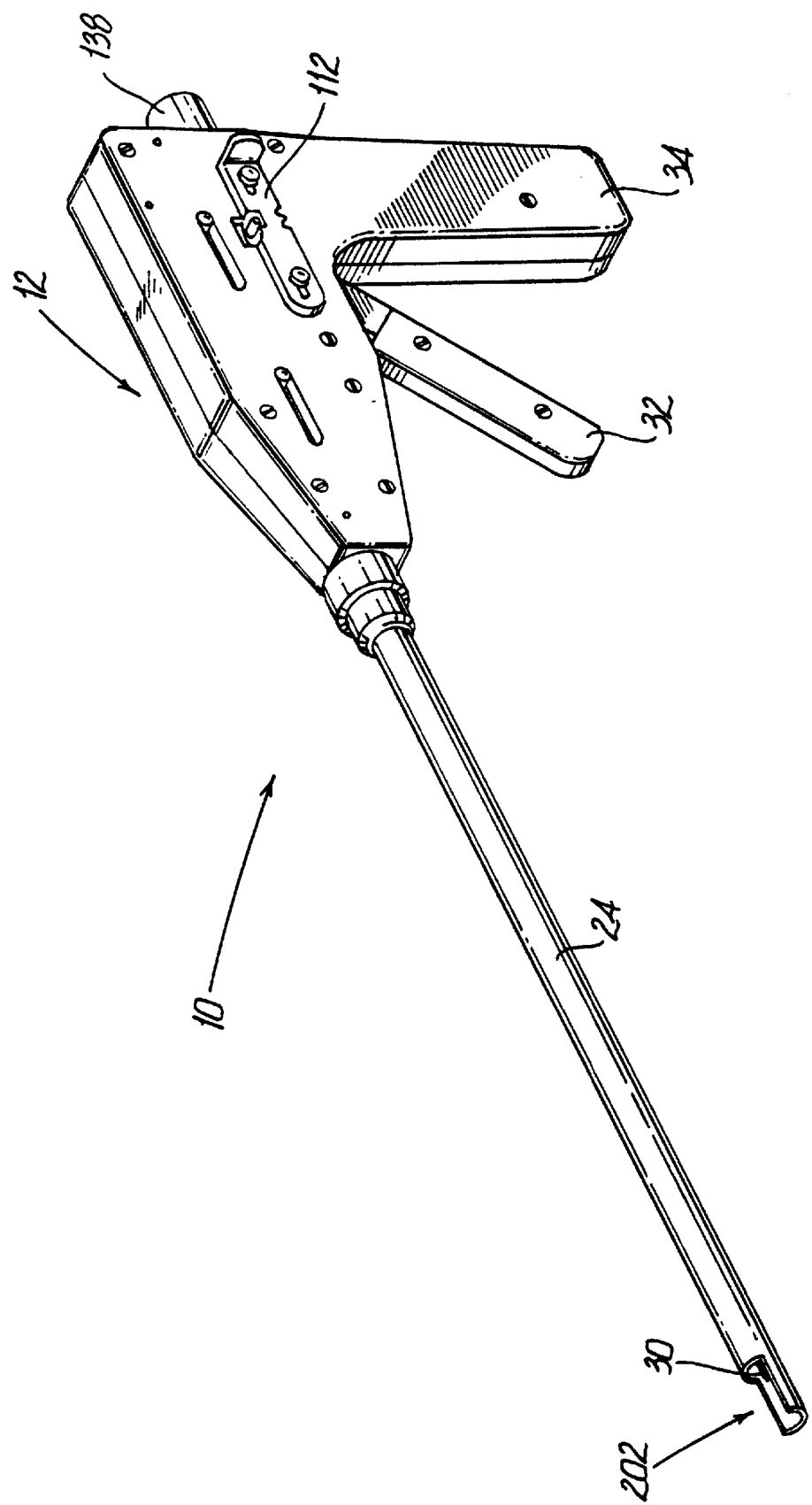
FIG. 1 illustrates a perspective view of a preferred embodiment of the device for applying surgical staples according to the present invention.

Referring in detail to the drawings, in which like reference numerals identify similar or identical elements throughout the views, FIG. 1 illustrates a first embodiment of the staple applying device shown generally as 10. A housing 12 is provided and encloses an internal frame having left and right halves 14 and 16, which are separated by front and rear spacers 18 and 20 as best seen in FIG. 2. Extending outwardly from housing 12 is an elongated tubular member 24 which encloses a pair of spaced, elongated shafts 26 and 28, as best seen FIGS. 2, 8 and 9. Device 10 is suitable for inserting a resorbable meniscal staple 30, which is removably held at the distal ends of shafts 26, 28, linearly into torn tissue such as the meniscus. A handle member 32 is pivotally movable toward and away handle member 34 to move shafts 26, 28 longitudinally as described hereinafter to insert meniscal staple 30 linearly into the meniscus.

Tubular member 24 allows the distal meniscal staple 30 to be inserted through a small incision in the body for placement within the meniscus or other similar bodily tissue to be repaired, thus allowing surgical procedures to be performed thereon without the need of severe incisions in adjacent body tissues.

Figure 4:
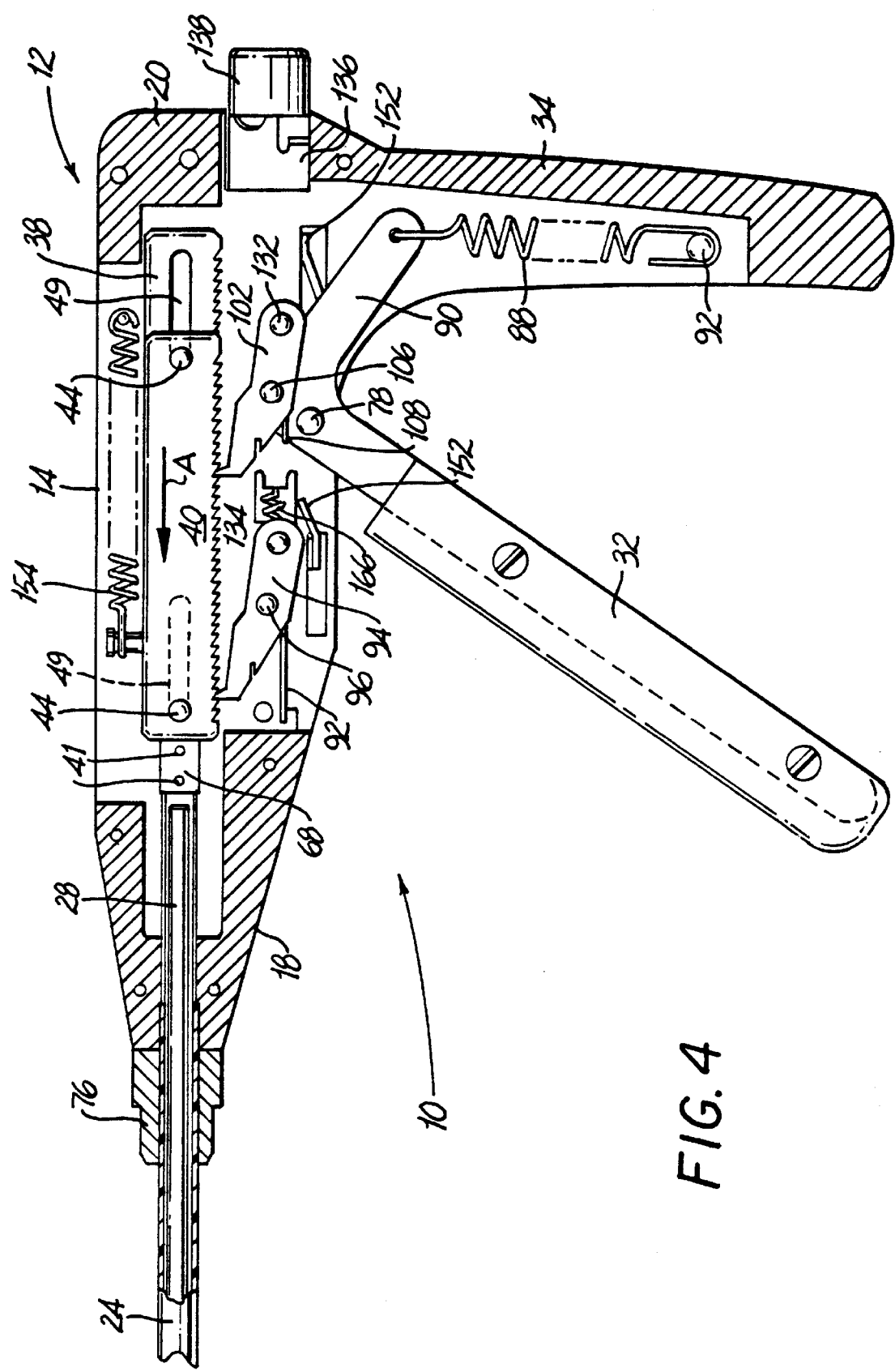
FIG. 4 illustrates a cut-away side view with the internal frame removed taken along lines 4—4 of FIG. 2.

Referring now to FIGS. 2 and 4, a pair of longitudinally movable elongated rack members 38 and 40 are positioned between frame halves 14 and 16. A pair of spaced pin members 44 project laterally from opposite sides of racks 38 and 40 through frame halves 14 and 16.

Figure 3:
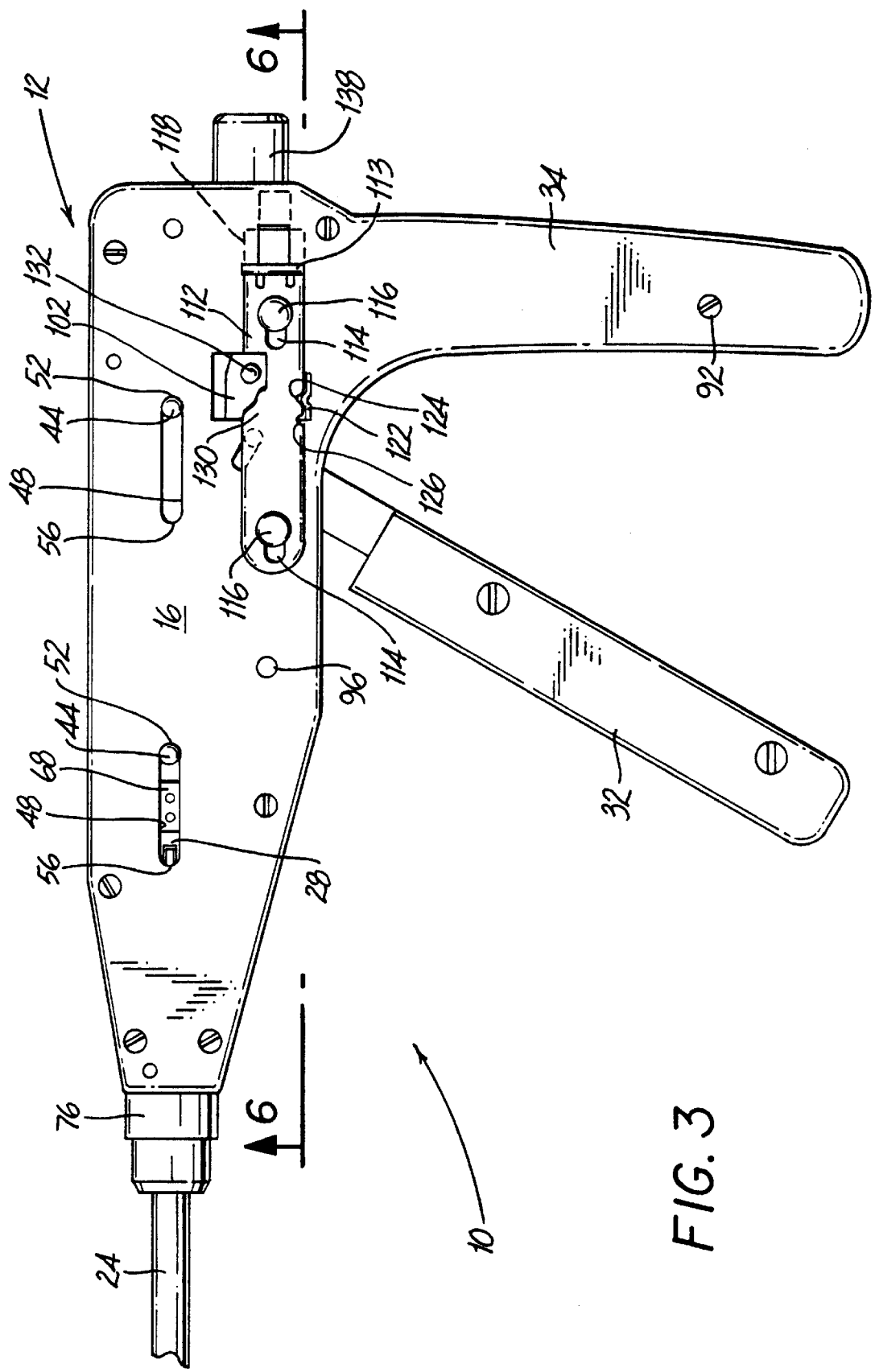
FIG. 3 illustrates a side cut-away view showing the internal frame of the device of FIG. 1.
Figure 5:
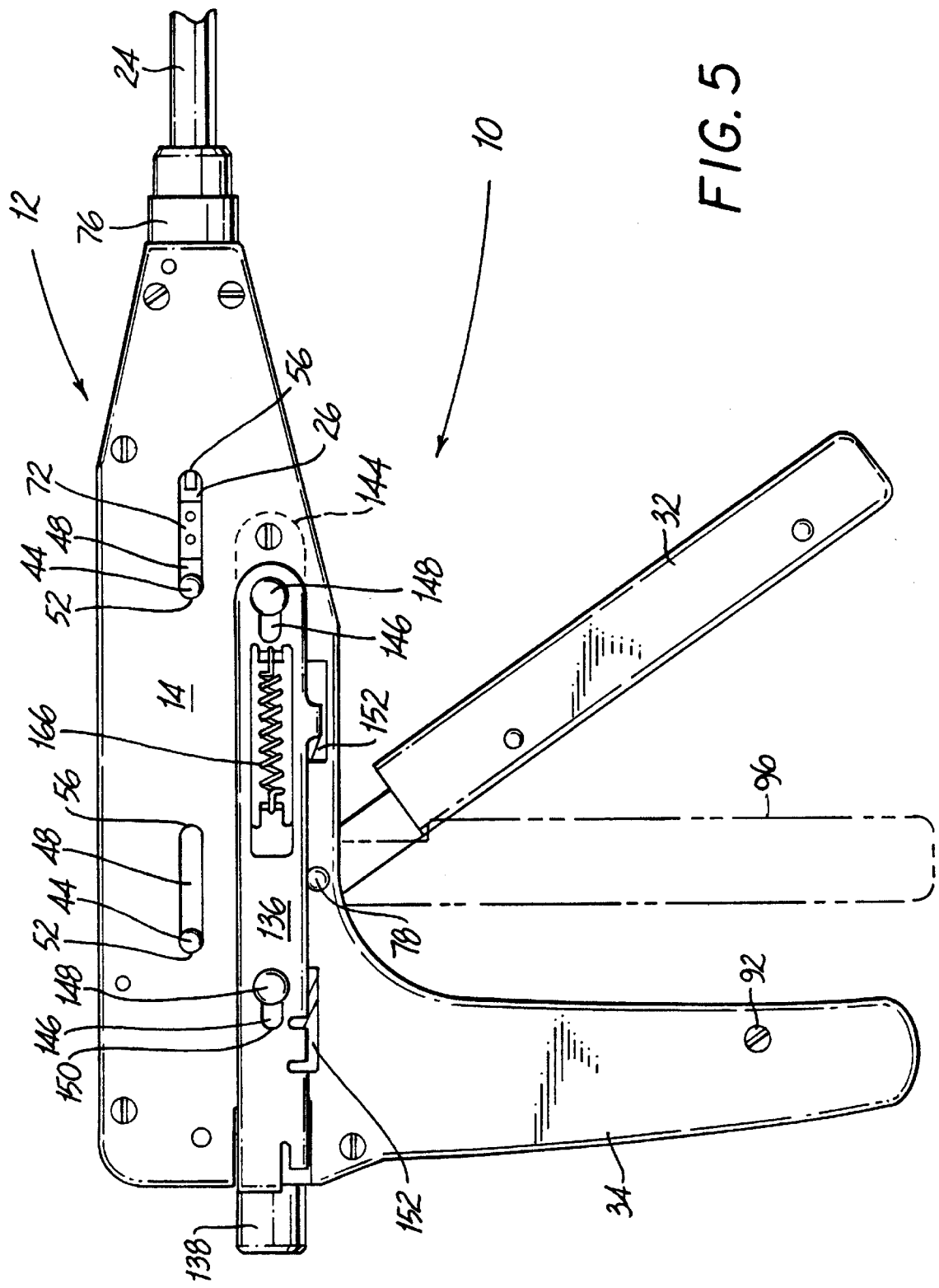
FIG. 5 illustrates a side view of the opposite side of the device in relation to FIG. 3 showing the internal frame of the device of FIG. 1.

Each pin member 44 slidably extends into an elongated slot 48 in frame halves 14 and 16, as shown in FIG. 3. Rack 40 is longitudinally movable between an initial rearward position, in which pin members 44 abut against the rearward shoulder portions 52 of slots 48 as shown in FIGS. 3 and 5, and a second forward position, in which pin members 44 abut against the forward shoulder portions 56 of slots 48. Rack 38 is provided with slots 49 similar to slots 48.

Shaft 28 extends longitudinally from the forward end of rack 40 so that shaft 28 moves longitudinally with rack 40 between an initial rearward position and a second forward position. Shaft 28 is attached to rack 40 by suitable means 41 such as pins, screws, rivets or the like which are retained within bores in the coupling portion 68 or rack 40. Similarly, shaft 26 extends longitudinally from the forward end of rack 38, as at coupling portion 72, so that shaft 26 moves longitudinally with rack 38 between an initial rearward position and a second forward position.

Front spacer 18 is provided with a bore through which tubular member 24 and shafts 26 and 28 longitudinally extend. A nose piece 76 located at the front end of spacer 18 surrounds tubular member 24, and provides additional support for tubular member 24.

Handle 32 is pivotally attached between frame halves 14, 16 by a pivot pin 78. A handle return spring 88 is connected between the end of a lateral extension 90 of handle 32 and an anchor pin 92 extending between frame halves 14, 16 of handle 34. Spring 88 returns handle 32 from its second position to its first position.

A pair of spaced front pawls 94, 95 engage with racks 40, 38, respectively, to prevent the rearward movement of racks 38, 40. Pawls 94, 95 are pivotally mounted between frame halves 14, 16 on a front pawl pin 96, which further maintains the spacing between pawls 94, 95. A spring member 98 biases the tongue end of pawls 94, 95 upward so that pawls 94, 95 engage racks 38, 40.

A pair of spaced rear pawls 102, 103 individually engage with racks 40, 38, respectively to selectively cause incremental forward longitudinal movement of racks 38, 40 in the direction of arrow A, as described hereinafter in relation to FIG. 4, when handle 32 is moved toward handle 34. Pawls 102, 103 are pivotally mounted between frame halves 14, 16 on a rear pawl pin 106, which is adapted to maintain the spacing between pawls 102, 103. A spring member 108 biases the tongue end of each pawl 102, 103 upward so that pawls 102, 103 individually engage its adjacent ratchet rack 38, 40. Together, pawls 102, 103 and racks 38, 40 provide a translating means for translating the pivotal motion of handle 32 toward handle 34 to incremental longitudinal motion to selectively move shafts 26, 28 longitudinally.

Referring to FIG. 3, a longitudinally movable elongated disconnect lever 112 is shown slidably mounted along the outer surface of frame half 16. Disconnect lever 112 is movable via finger pressure, which may be applied against a thumb piece 113, which may extend outside of housing 12 and extend laterally from disconnect lever 112. Disconnect lever 112 is provided with a pair of spaced, longitudinally aligned, elongated slots 114. A shoulder pin 116 extends laterally from frame half 16 through each slot 114. Together, shoulder pins 116 and slots 114 limit the longitudinal movement of disconnect lever 112 between a forward position as shown in FIG. 3, in which pines 116 abut against rear shoulder portions of slots 114, and a rearward position, as indicated by phantom lines 118 in which pines 116 abut against front shoulder portions of slots 114.

A spring detent 122 extends outwardly from the side of frame half 16. Disconnect lever 112 is provided with a pair of spaced recesses 124 and 126 along its lower surface. When disconnect lever 112 is moved to its first or initial forward position, spring detent 122 engages with rear recess 124 to retain disconnect lever 112 in the position shown in FIG. 3. When disconnect lever 112 is moved rearwardly from the forward position to the rearward position, detent 122 engages with front recess 126 to retain disconnect lever 112 in the rearward position.

Disconnect lever 112 is movable between its initial position and its second rear position. In the initial position as shown in FIG. 3, disconnect lever 112 allows both rear pawls 102, 103 to engage racks 40, 38, respectively to translate the pivotal motion of handle 32 toward handle 34 to longitudinal motion to move both racks 38, 40 and shafts 26, 28 longitudinally forward. FIG. 4 shows rear pawl 102 engaging rack 40. In its second rear position, disconnect lever 112 disengages right rear pawl 102 from rack 40. Thus, the pivotal motion of handle 32 toward handle 34 is translated to only move rack 38 and shaft 26 longitudinally forward. To achieve this disengagement of right rear pawl 102 from rack 40 a cam shoulder 130 formed on level 112 is provided which engages a disconnect pin 132, which extends laterally from pawl 102, to move the rearward end of pawl 102 upward. The upward movement of the rearward end of pawl 102 disengages the forward tongue end 134 of pawl 102 from rack 38.

Referring to FIG. 5, a longitudinally movable elongated release lever 136 is slidably mounted on the outer surface of frame half 14. Release lever 136 is movable via finger pressure applied against a release button 138 positioned adjacent the rear of housing 12. Release lever 136 is movable longitudinally between an initial rear position and a second forward position, as indicated by phantom lines 144, and is provided with a pair of spaced, longitudinally aligned, elongated slots 146. A shoulder pin 148 extends laterally from frame half 14 through each slot 146. Together, shoulder pins 148 and slots 146 limit the longitudinal movement of release lever 136 between a rear position, as shown in FIG. 5, in which pins 148 abut against forward shoulder portions of slots 146, and a forward position in which pins 148 abut against rear shoulder portions of slots 146.

Release lever 136 is movable to its forward position via finger pressure to disengage front and rear pawls 94, 95 and 102, 103 from racks 40, 38. This allows racks 38, 40 to be returned rearwardly to their initial positions. In order that release lever 136 may disengage pawls 94, 95 and 102, 103 from racks 40, 38, release lever 136 is provided with a pair of spaced cam extensions 152, which extend laterally from release lever 136. When release lever 136 is moved to its forward position, cam extensions 152 engage against the bottom rearward end portions of pawls 94, 95 and 102, 103 to move the rearward ends of pawls 94, 95 and 102, 103 upward. This pivots the pawls to disengage the forward tongue ends of pawls 94, 95 and 102, 103 from racks 40, 38 to releas the racks 40, 38 for longitudinal rearward movement.

Return springs 154 and 160, as seen in FIG. 2, are connected to racks 40 and 38, respectively, and pin 46. Return springs 154 and 160 return racks 38 and 40 rearwardly to an initial position when pawls 94, 95 and 102, 103 are disengaged. The movement of racks 38, 40 rearwardly to their initial position returns shafts 26, 28 to their initial position. When release lever 136 is released, a biasing spring 166 returns lever 136 to its initial rear position.

Referring to FIG. 9, each shaft 26, 28 may be segmented to include push pin segments 174 and push bar segments 182 which are ultimately connected to elongated needle holders 178. Of course, shafts 26 and 28 may be single rod-like members if desired. A clip member 186 may be provided to join push bars 182 to needle holders 178 in a detachable manner as shown in FIG. 8, whereby clip 186 engages and retains a ball 188, which extends axially from the rearward end of the needle holder 178.

At the distal end of each shaft 26, 28 is an elongated needle member 190 which extends longitudinally from an end portion of each needle holder 178. As described in detail below, staple 30 includes a pair of resorbable anchor segments 194 joined at their rear portions by a resorbable flexible web 198, which may preferably be in the form of a suture. Each anchor segment 194 may be provided with a plurality of barb-like projections 206 for anchoring the staple 30 in the tissue to which it is applied. Anchor segment 194 further includes an elongated channel or groove along its length which receives the needle 190. Each channel and needle 190 cooperate so that longitudinal forward movement of shafts 26, 28 in the direction of arrow B advances anchor segments 194 forwardly. Needles 190 are releasable from the channels when shafts 26, 28 are withdrawn longitudinally rearward, thus allowing needles 190 to be withdrawn rearwardly from anchor segments 194 while staple 30 remains in the tissue.

Referring to FIG. 7, the distal end of tubular member 24 is provided with a notch 202, which allows for loading of staple 30 and further allows visual observation of the anchor segments 194 of staple 30 by the surgeon during positioning of staple 30 within the meniscus to be repaired. Notch 202 provides for rotatable orientation of tubular member 24 to align staple 30 with the tear in the meniscal tissue.

In use, tubular member 24 is inserted through an incision and, with the aid of an endoscope or arthroscope, the surgeon positions the distal tip 204 of tubular member 24 adjacent the meniscal tissue to be repaired.

When handles 32, 34 are squeezed together, both rear pawls 102, 103 are pivoted to move left and right ratchet racks 38, 40 longitudinally forward in the direction of arrow A, as shown in FIG. 4. Springs 108 bias the forward ends of pawls 102, 103 upward, causing pawls 102, 103 to engage with ratchet racks 38, 40. Consequently, the forward motion of rear pawls 102, 103 causes ratchet racks 38, 40 to move distally forward under the influence of the forward pivotal movements of pawls 102, 103. As may be appreciated forward pawls 94, 95, which remain engaged with racks 38, 40 during the return motion of handle 32, prevent rack return springs 154, 160 from prematurely moving racks 38, 40 rearwardly as handles 32, 34 are repeatedly squeezed and released to incrementally advance ratchet racks 28, 40 longitudinally forward.

In the initial position of shafts 26, 28, one needle 190 is positioned ahead of the other needle 190 so that movement of ratchet racks 38, 40 causes one anchor segment 194 of staple 30 to advance linearly ahead of the other anchor segment 194. After sufficient distal movement of the shafts 26, 28 to position the first anchor segment 194 fully into the meniscal tissue, disconnect lever 122 may now be actuated rearwardly under the influence of finger pressure from its initial position to its second rearward position to disengage right rear pawl 102 from ratchet rack 40. As discussed in detail above, spring detent 122 retains disconnect lever 112 in its initial position and its second position. Consequently, further squeezing of handle 32 toward handle 34 will only cause distal forward longitudinal movement of left ratchet rack 38 to linearly advance the trailing anchor segment 194 into the meniscus. The disengagement of right rear pawl 102 from ratchet rack 40 prevents further longitudinal movement of the first anchor segment 194 linearly into the meniscus.

After both anchor segments 194 are inserted and anchored in the desired position by the barb-like projections 206 with web 198 positioned accurately across the tear in the meniscus, release button 138 may be pressed inwardly to disengage front and rear pawls 94, 95, and 103 from ratchet racks 38, 40 and thereby allow ratchet racks 38, 40 to move rearward to their original initial position under the influence of return springs 154, 160.

Pressing inward on release button 138 causes release lever 136 to move distally forward and causes lateral cam extensions 152 to engage against the rearward portions of pawls 94, 95 and 103 and rotate pawls 94, 95 and 103 to disengage their forward tongue ends from racks 38, 40, thus allowing return springs 154, 160 to return racks 38, 40 and shafts 26, 28 longitudinally to their initial position.

Return of shafts 26, 28 to their initial position pulls the needles 190 rearwardly out of the channels of anchor segments 194 and withdraws needles 190 from the tissue. The barb-like projections 206 along anchor segments 194 retain staple 30 in the meniscus, with web 198 held across the tear in the meniscus. Tubular member 24 may then be withdrawn from the incision.

Turning now to FIG. 10, there is shown an alternate embodiment of the repair device 300 of the present invention. Repair device 10 generally comprises a pair of needles 302, preferably constructed of stainless steel or other surgical grade metal alloy, having a sharp tip 303 at one end to facilitate penetration through tissue, and a blunt end 305 at the other end. In this embodiment, along with the other preferred embodiments described hereafter, the length of each needle is between 6 inches and 10 inches. However, this is not intended to be limiting, as clearly needles of various lengths may be utilized.

Engaged with needles 302 are a pair of anchoring or connecting leg members 304 which are similar to anchor segments 194 described above. Anchoring member 304 are constructed of a bioresorbable material, such as homopolymers and copolymers of lactide, glycolide, pplydioxanone, trimethylene carbonate, polyethylene oxide or other bioabsorbable materials or blends of these copolymers. Preferably, the anchoring members 304 are injection molded and are formed of a copolymer of lactide and glycolide. Anchor members 304 are linked by a flexible material 306 such as a suture, also constructed of a bioresorbable material, such as a lactide/glycolide copolymer. Flexible material 306 is similar to web 198 described above and allows for movement of anchoring members 304 with respect to one another. Anchor members 304 of this embodiment, along with the other preferred embodiments described hereafter, preferably have a length of between about 0.25 inch and 2 inches. However, this is not intended to be limiting as clearly anchor members of various lengths may be utilized. Flexible material 306 of this embodiment, along with the other preferred embodiments described hereafter, preferably has a length of between about 0.25 inch and 2 inches. Likewise, this is not intended to be limiting as clearly flexible material of various lengths may be utilized.

Figure 11:
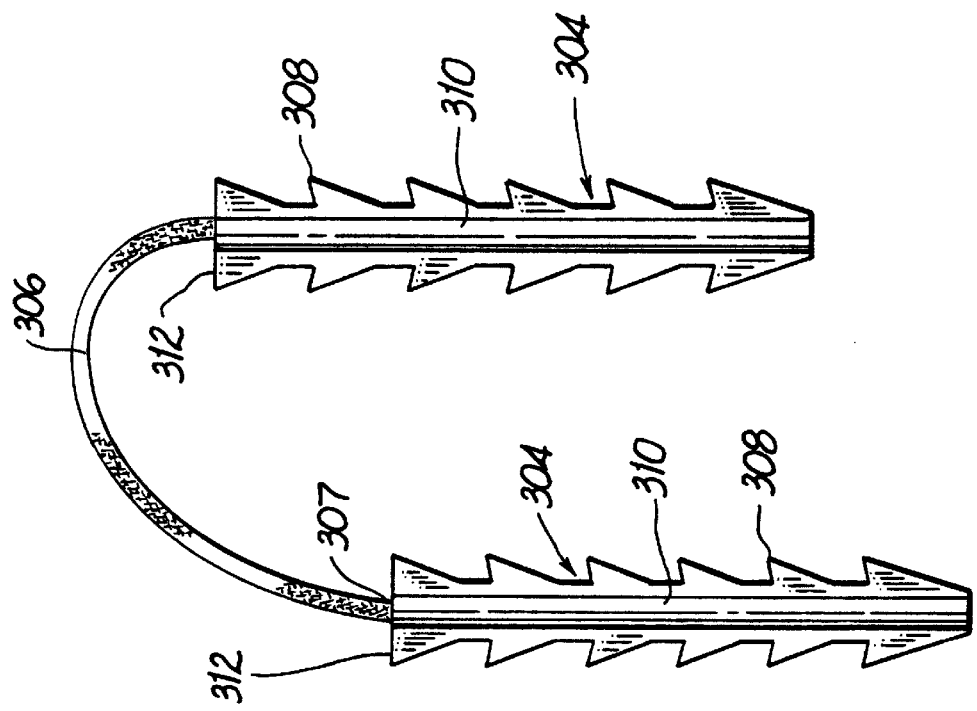
FIG. 11 illustrates a side view of the connecting members of the embodiment of FIG. 10 along with their suture interconnection.

Needles 302 provide a piercing means that is engaged with anchor members 304 as discussed in detail hereafter so that a pushing force applied axially to needles 302 in a first direction is transmitted to anchor members 304 to advance anchor members 304 into the torn tissue, while a second pulling force applied in the opposite direction to the initial pushing force releases needles 302 from their engagement with anchoring members 304. As best seen in FIG. 11, anchor members 304 are secured to suture 306 as a joint 307 by suitable means such as insert molding.

Anchor members 304 are provided with an anchoring means in the form of a plurality of barb-like projections 308 which serve to anchor device 300 in the tissue to be repaired. Barbs 308 have a tapered shape to allow anchor members 304 to be pushed through tissue or muscle, such as the meniscus of the knee, in a first forward direction and to prevent anchor members 304 from traveling in a reverse or opposite direction. As may be appreciated, barb-like projections 308 may taper rearwardly toward the penetration end of anchoring members 304 to facilitate movement of tissue anchoring members 304 forwardly through the tissue. Although as shown in FIG. 10 six barbs 308 are provided, any number may be provided, so long as the barbs penetrate the tissue to anchor the device 300. Similarly, with the other embodiments hereafter described, the number of barbs is also six, although any number of barbs may likewise be provided, so long as the barbs penetrate the tissue to anchor the device.

Figure 15:
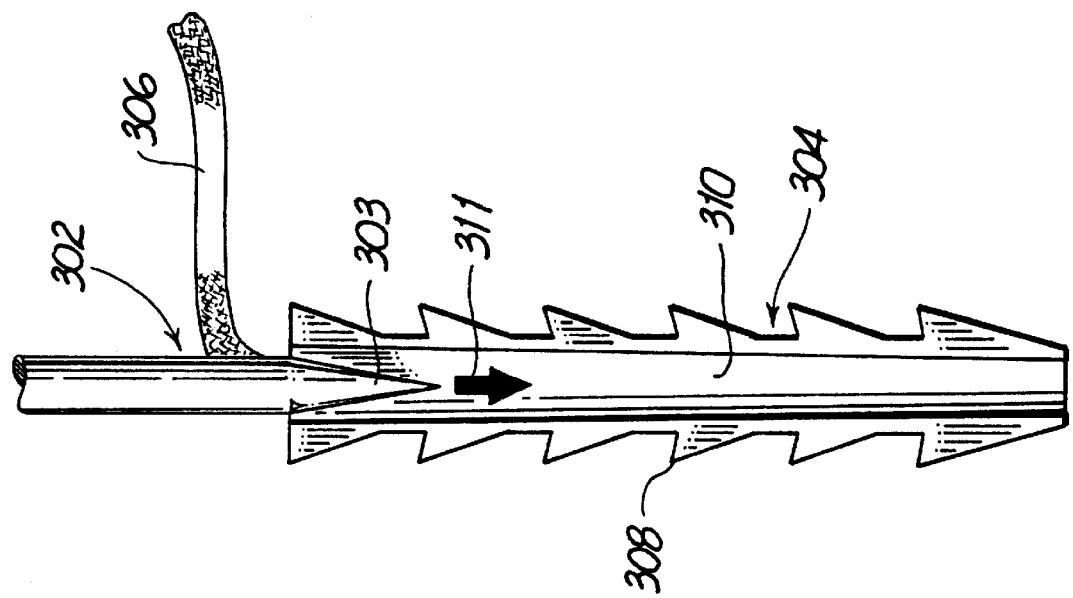
FIG. 15 illustrates a side view of one of the connecting members of the embodiment of FIG. 10 showing the entry of the needle as it is being inserted into the channel of the connecting member.
Figure 21:
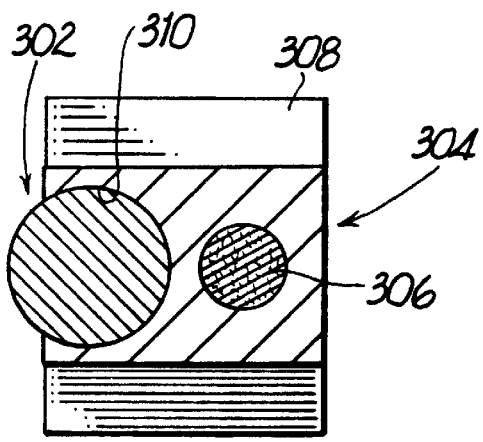
FIG. 21 illustrates a cross-sectional view of the embodiments of FIGS. 10, and 16–19.
Figure 22:
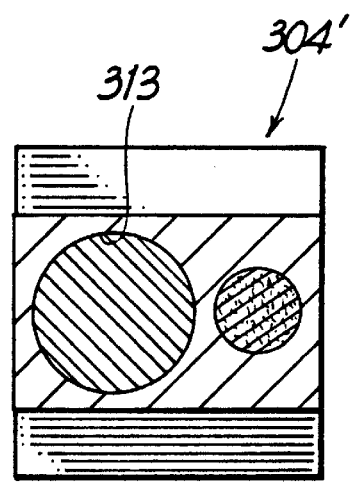
FIG. 22 illustrates a cross-sectional view of an additional alternative embodiment.

Referring to FIG. 11, each anchor member 304 is provided with a channel 310 which may extend laterally into the body of each anchor member 304 along the length of anchor member 304. Preferably, each channel 310 has a cross section which may be circular. Further, as shown in detail in FIG. 21, it is preferred that each channel 310 intersect with one of the sides of anchor member 304 so that each channel 310 may be exposed narrowly along its longitudinal length to reduce the thickness of each anchor member 304. As best shown in FIG. 10, one of the needles 302 is positioned longitudinally in each of the channels 310, and may be retained therein, exposed along the open length of channel 310. Alternatively as shown in detail in FIG. 22, the channel may instead be a bore 313 that extends longitudinally through the body 304' of each anchor member. Referring to FIG. 15, channel 310 allows for needles 302 to be inserted in anchor member 304 in the direction of arrow 311 so that the sharp penetration tip 303 of needle 302 protrudes outwardly from the body of anchor member 304 as shown in FIG. 10 to provide a penetration end for anchor member 304.

As shown in FIG. 11, channel 310 extends longitudinally from the trailing or distal end 312 of each anchor member 304 opposite the penetration or proximate end of each anchor member 304. A means of engagement is provided between needles 302 and anchoring members 304 so that anchoring members 304 may be carried forward by needles 302 as they are inserted forward into the tissues of the body. The means of engagement may be provided by a frictional engagement between channel 310 in anchoring members 304 and the needle 302 positioned longitudinally therein. In this embodiment, each channel 310 may have a uniform cross section, and needles 302 may likewise have a uniform cross-section, with each channel 310 having a narrower uniform cross section to provide a frictional engagement with needle 302 therein. Consequently, a first pushing force applied axially to the needles 302 is transmitted to anchoring members 304 to advance anchoring members 304 into the torn tissue, while a second pulling force applied in the opposite direction to the pushing force releases the needles from their engagement with the anchoring members. The pulling force applied rearwards to needles 302, overcomes the frictional engagement between needles 302 and anchor members 304, thus releasing needles 302 from the anchoring members 304.

Figure 12:
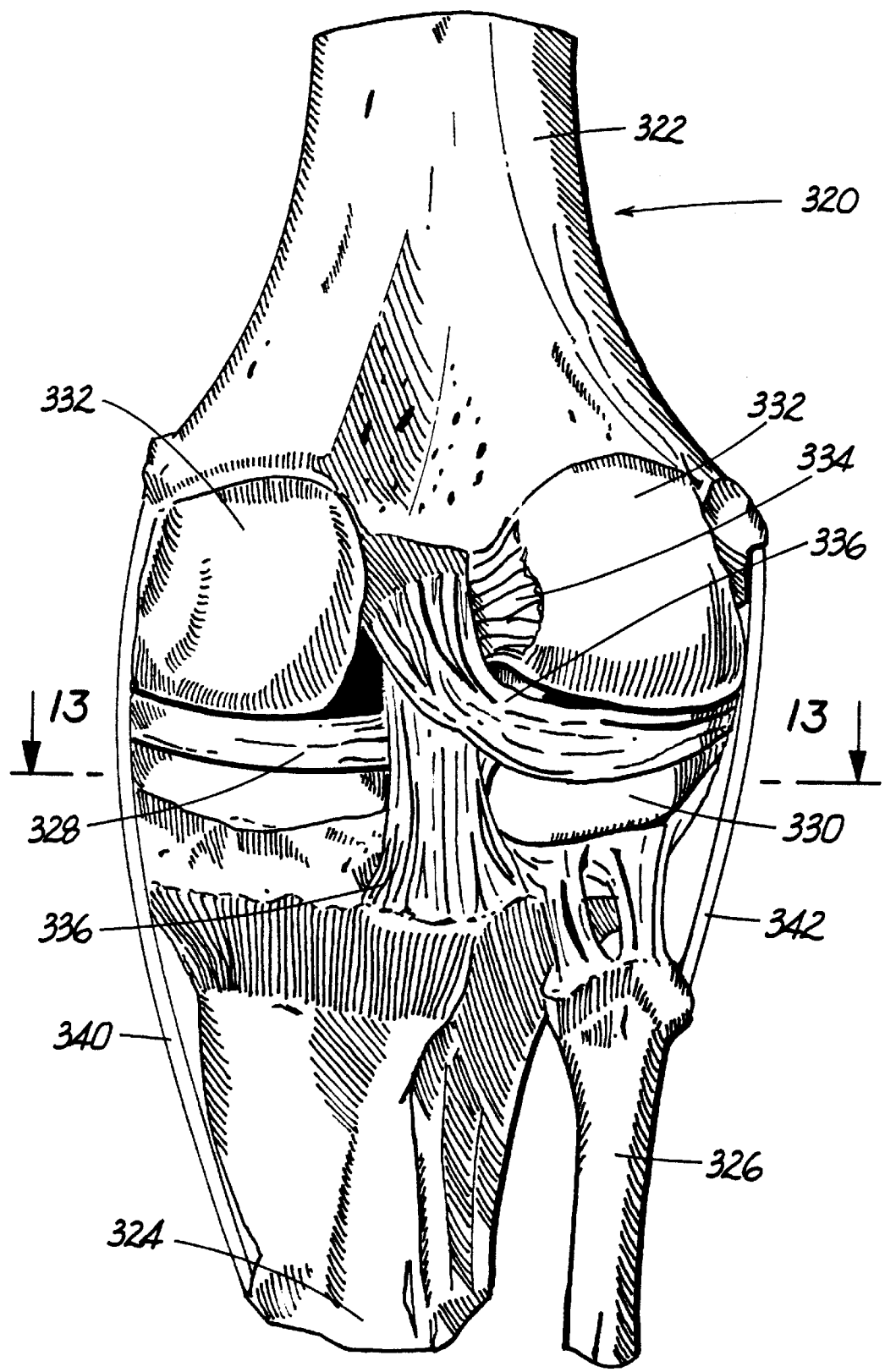
FIG. 12 illustrates a perspective posterior view of the muscular structure of the knee.

FIG. 12 illustrates the muscular and ligament structure of the knee 320, including the pertinent components of the knee to which the present invention is directed. As is well known, the femur 322 is joined to tibia 324 and fibula 326 by muscles, tendons and ligaments, and these bones are separated and cushioned by the medial meniscus 328 and lateral meniscus 330. Condyles 332 of femur 322 rest on the meniscus, and the bones are joined and supported by anterior cruciate ligament 334, ligament of Wrisberg 338, posterior cruciate ligament 336, and transverse ligament 338 (see FIG. 14). The joint capsule is formed by tibial collateral ligament 340 and fibular collateral ligament 342.

Figure 13:
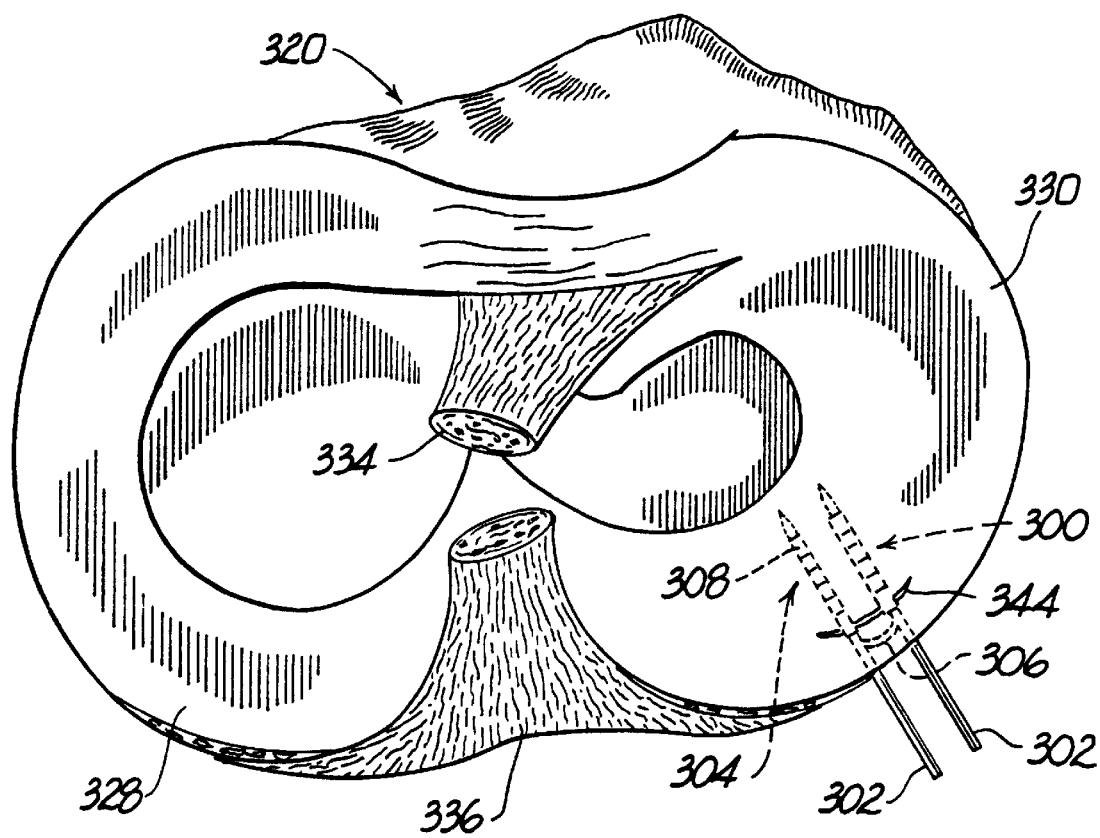
FIG. 13 illustrates a cut-away perspective view of the knee of FIG. 12 along line 13—13 showing the device according to FIG. 10 in position during the meniscal repair procedure.
Figure 14:
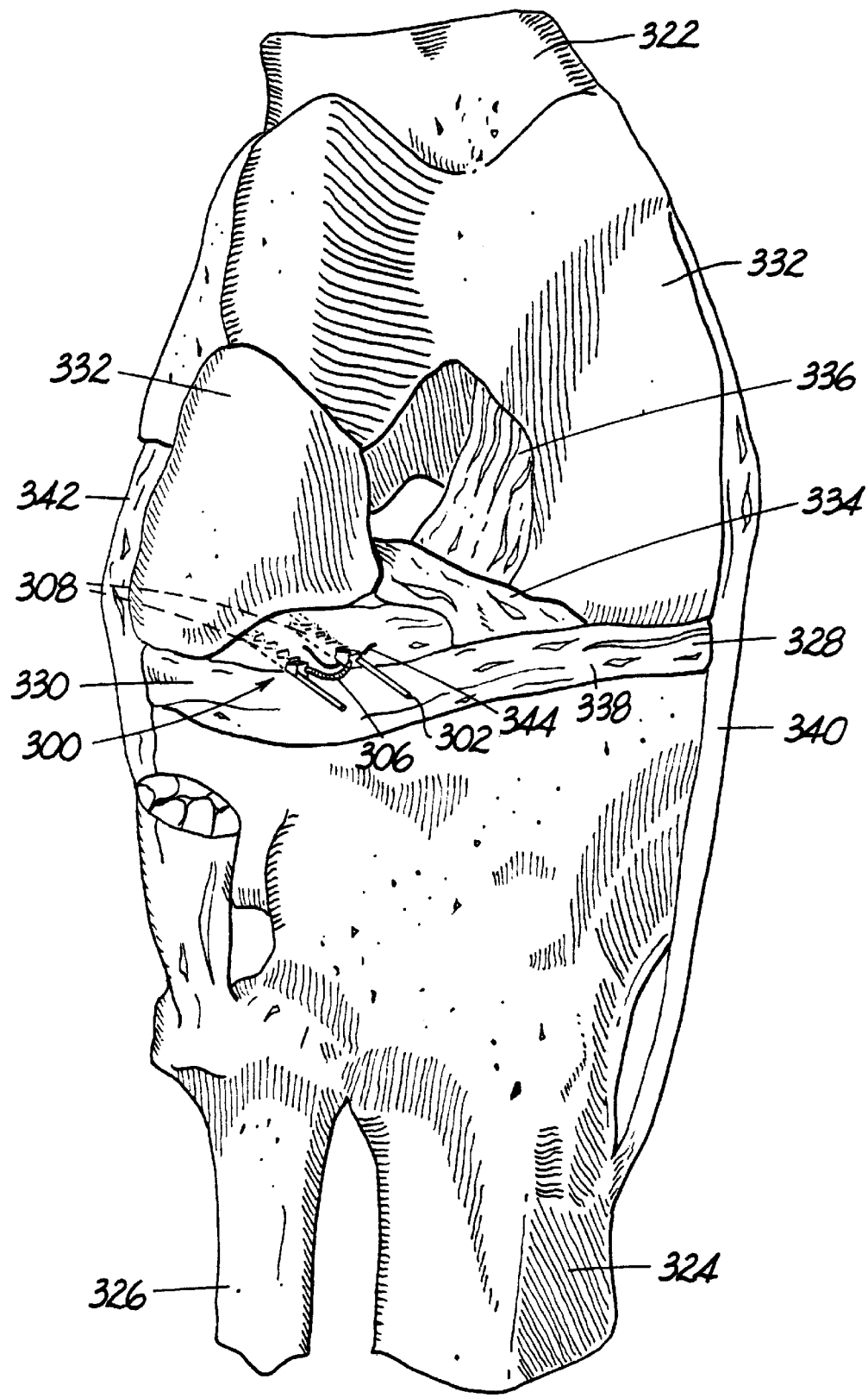
FIG. 14 illustrates a perspective anterior view of the knee of FIG. 12 with the device according to FIG. 10 in position during the meniscal repair procedure.

FIGS. 13 and 14 illustrate the device 300 of the present invention in use, with FIG. 13 showing knee 320 along lines 13—13 of FIG. 12. During arthroscopic surgery, a surgeon will make an incision in the skin and tissue in the area of the knee to be repaired. The lateral meniscus 330 of a knee 320 having a tear 344 is repaired with the present invention by inserting the device and pushing needles 302 through the meniscus on one side of the tear, and through the torn region. The engagement between needles 302 and anchor members 304 advances anchor members 304 and their barb-like projections 308 into the tissue as needles 302 are pushed forward in a first direction along the axis of the needles. Continued pushing on needles 302 will advance anchor members 304 into the tissue and suture 306 across the tear.

When flexible member 306 becomes substantially flush with meniscus 330 and is pulled taut, pushing is discontinued. Barbs 308 of anchor members 304 anchor the device in the meniscus 330 and prevent the device from backing off, so that tear 344 is maintained in an abutting relationship against itself to facilitate healing.

Needles 302 may then be removed from anchoring members 304 by a second pulling motion applied to the needles in the opposite direction to the pushing force, thus releasing needles 302 from the anchoring members 304 while allowing anchor members 304 to remain in position in the tissue of the body with suture 306 substantially flush with meniscus 330. Consequently, tear 344 is maintained in its abutting relationship against itself to facilitate healing. The material of which anchor members 304 and suture 306 are constructed are preferably bio-resorbable materials that are resorbed at a rate which is slow enough to facilitate healing of the tear in the tissue. After removal of needles 302, the incision is stitched closed.

Turning now to FIG. 17, another embodiment 350 of the invention is shown. Device 350 includes a pair of elongated needles 302, a pair of elongated anchor members 352 similar to anchor members 304 that are joined by a flexible member or suture 306. Barb-like projections 308 protrude from anchor members 352. Device 350 also includes an elongated channel 354 that extends laterally into each anchor member 352 from the trailing or proximal end 312 opposite the penetration or distal end 356 of each anchor member 352. One of the needles 302 is positioned longitudinally in each of the channels 354. Needles 302 are provided with an essentially constant diameter, while channel 354 tapers or narrows in the direction of the penetration end 356 to a cross sectional area somewhat less than the diameter of needles 302. Accordingly, anchor members 352 and needles 302 may be provided with a suitable frictional engagement that is sufficient to allow anchor members 352 and their barb-like projections 308 to be advanced into the tissue as needles 302 are pushed forward in a first direction. The frictional engagement between anchor members 352 and needles 302 may be overcome by a second pulling force applied to needles 302 in the opposite direction as the pushing force while allowing anchor members 352 to remain in position in the tissue of the body with the suture 306 contacting the tissue adjacent the tear.

Referring to FIG. 18, there is shown a further embodiment 360 of the device of the present invention. Device 360 includes a pair of elongated needles 302, a pair of elongated anchor members 362 similar to elongated anchor members 304 that are joined by a flexible member or suture 306 barb-like projections 308. As shown in the figure, device 360 also includes an elongated channel 364. Channel 364 has an essentially constant cross sectional area, and needles 302 taper or narrow in the direction of their penetration ends 303.

Turning now to FIG. 19, an additional embodiment 370 of the present invention is shown. Device 370 similarly includes a pair of elongated needles 302 a pair of elongated anchor members 372 that are joined by a flexible member or suture 306 and a plurality of barb-like projections 308. As shown in the figure, device 370 also includes an elongated channel 374 that extends laterally into each anchor member 372. Each channel 374 may taper or narrow from the trailing or distal end in the direction of the penetration end of the anchor member, and each needle 302 has a corresponding taper in the direction of its sharp penetrating tip 303. When needle 302 is pushed in the axial direction, needle 302 and anchor member 372 have an abutting relationship along the length of channel 374, which evenly transmits the pushing force applied to needle 302 to anchor member 372.

Referring to FIG. 20, a further embodiment 380 of the present invention is shown. Device 380 includes a pair of elongated needles 302, a pair of elongated anchor members 382 similar to elongated anchor members 304 that are joined by a flexible member or suture 306 and include a plurality of barb-like projections 308. As shown in the figure, device 380 also includes an elongated channel 384 that extends laterally into each anchor member 382 from the trailing or distal end 386. Each channel 384 may have an essentially constant cross section, and each needle 302 may be provided with a shoulder 388 a suitable distance from its sharp penetration tip 303. Trailing end 386 provides an abutment surface against which shoulder 388 may abut. When needles 302 are pushed in the axial direction, shoulders 388 abut against trailing end 386, thus allowing the pushing force applied to needle 302 to be transmitted to anchor members 382.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A tissue tear repair device for repairing torn tissue in a patient, comprising:
   a pair of tissue anchoring members, each anchoring member having a central longitudinal axis and having a proximal end and a distal end;
   a flexible member having a first and fixedly connected adjacent the promixal end of one of said anchoring members and a second end fixedly connected adjacent the proximal end of the other of said anchoring members, each of the first and second ends of the flexible member being connected to the anchoring members at a location offset from the central longitudinal axis of the anchoring member such that the proximal end of each of the anchoring members includes an unobstructed tool engaging surface;
   a channel extending over a length of each anchoring member; and
   a needle positioned in each channel.

2. The tissue tear repair device of claim 1, wherein each channel has an essentially uniform cross section.

3. The tissue tear repair device of claim 1, wherein each needle includes a shoulder for engaging an end of said anchoring member opposite a penetration end of the needle.

4. The tissue tear repair device of claim 1, wherein said flexible member comprises a resorbable suture.

5. The tissue tear repair device of claim 1, wherein said anchoring members include a plurality of barb-like portions disposed along a length of said anchoring member.

6. The tissue tear repair device of claim 5, wherein said barb-like portions have a tapered shape to permit penetration into tissue, but prevent movement in a reverse direction.

7. The tissue repair device of claim 1, wherein the first end of the flexible member is fixedly connected to the proximal end of one of the pair of anchoring members at a location offset from a centerline of the one anchoring member, and the second end of the flexible member is fixedly connected to the proximal end of the other of the pair of anchoring members at a location offset from the centerline of the other anchoring member.

8. A tissue repair device for repairing torn tissue, comprising:
   a pair of tissue connecting members having a central longitudinal axis each of said connecting members having a penetration end, an opposite trailing end proximal of said penetration end, and a channel extending over a length of each of said connecting members;
   a plurality of barb-like portions disposed along each of said connecting members for retaining each of said connecting members in torn tissue; and
   a flexible member having a first end connected adjacent the trailing end of one of said connecting members and a second end connected adjacent the trailing end of the other of said connecting members, each of the first and second ends of the flexible member being connected at a location offset from the central longitudinal axis of the connecting member such that the trailing end of each connecting member includes an unobstructed tool engaging surface.

9. A tissue tear repair device for repairing torn tissue in a patient, comprising:
   a pair of tissue anchoring members;
   a flexible member having a first end fixedly connected to one of said anchoring members and a second end fixedly connected to the other of said anchoring members;

a channel extending over a length of each anchoring member; and a needle positioned in each channel, wherein each channel tapers in the direction of a penetration end of said needles.

10. A tissue tear repair device comprising:

a pair of anchoring members, each anchoring member having a distal penetration end configured to penetrate body tissue;

a channel extending over a length of each of the anchoring members;

a plurality of barb-like portions disposed along each of the anchoring members; and a flexible member interconnecting the anchoring members, wherein the anchoring members are connected to facilitate penetration of body tissue from a common direction, wherein each of the channels tapers in the direction of the penetration end of the anchoring member.

* * * * *